US010363292B2

(12) United States Patent
Li et al.

(10) Patent No.: US 10,363,292 B2
(45) Date of Patent: Jul. 30, 2019

(54) VACCINATION WITH ANTI-TICK ANTIGENS TO CONTROL MULTIPLE TICK SPECIES AND DISEASE TRANSMISSION IN WHITE-TAILED DEER AND OTHER HOST ANIMALS

(71) Applicants: The United States of America, as represented by the Secretary of Agriculture, Washington, DC (US); LOUISIANA STATE UNIVERSITY

(72) Inventors: Andrew Y. Li, Ellicott City, MD (US); Felicito Guerrero, Boerne, TX (US); Lane D. Foil, Baton Rouge, LA (US); Adalberto A. Perez De Leon, Kerrville, TX (US)

(73) Assignees: The United States of America, as Represented by the Secretary of Agriculture, Washington, DC (US); Board of Supervisors of Louisiana State University and Agriculture and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/706,895

(22) Filed: Sep. 18, 2017

(65) Prior Publication Data

US 2018/0085443 A1    Mar. 29, 2018

Related U.S. Application Data

(60) Provisional application No. 62/398,706, filed on Sep. 23, 2016.

(51) Int. Cl.
*A61K 39/00* (2006.01)

(52) U.S. Cl.
CPC ...... *A61K 39/0003* (2013.01); *A61K 2039/53* (2013.01); *A61K 2039/552* (2013.01); *A61K 2039/55566* (2013.01); *A61K 2039/58* (2013.01)

(58) Field of Classification Search
None
See application file for complete search history.

(56) References Cited

PUBLICATIONS

Carreon et al. 2012 (Vaccination with BM86, subolesin and akirin protective antigens for the control of tick infestations in white tailed deer and red deer; Vaccine 30: 273-279) (Year: 2012).*
Freeman et al. 2010 (Bm86 midgut protein sequence variation in South Texas cattle fever ticks; Parasites & Vectors 3:101). (Year: 2010).*
Khan 2013 (DNA vaccines: roles against disease; Germs 3(1):26). (Year: 2013).*
Merino et al. 2013 (Tick vaccines and the control of tick-borne pathogens; Cellular and Infection Microbiology; vol. 3, article 30) (Year: 2013).*

* cited by examiner

*Primary Examiner* — Mary Maille Lyons
(74) *Attorney, Agent, or Firm* — John Fado; Ariel Atkinson

(57) ABSTRACT

Compositions of either the Rm86Texas protein from a Texas outbreak strain of the southern cattle fever tick, *Rhipicephalus microplus*, or a nucleic acid construct incorporating a nucleic acid sequence encoding this Rm86Texas protein, are effective for eliciting a protective immune response in non-bovine animals. The Rm86Texas protein is immunogenic and can be administered as a protein vaccine, or in the alternative, the nucleic acid construct can be utilized as a DNA vaccine. Induction of the immune response significantly reduces or eliminates the infestation of treated, non-bovine animals with ticks. Moreover, as ticks are vectors of a variety of pathogens, the reduction in the incidence of tick infestation afforded by the vaccines may concurrently reduce the incidence of diseases caused by these pathogens in susceptible animals.

10 Claims, 6 Drawing Sheets
Specification includes a Sequence Listing.

```
Rm86TX    1    MRGIALFVAAVSLIVECTAESSICSDFGNEFCRNAECEVVPGAEDDFVCK    50
Bm86TICK  1    :::::::::::::::::::G::::::::::::::::::::::::::::::    50
Bm86GAV   1                  :::::::::::::::::::::::::::::::             31

Rm86TX    51   CPRDNMYFNAAEKQCEYKDTCKTRECSYGRCVESNPSKGSCVCEASDDLT   100
Bm86TICK  51   ::::::::::::::::::::::::::::::::::::::::::A:::::::   100
Bm86GAV   32   ::::::::::::::::::::::::::::::::::::::::::A:::::::   81

Rm86TX    101  LQCKIKNDFATDCRNRGGTAKLRTDGFIGATCDCGEWGAMNKTTRNCVPT   150
Bm86TICK  101  ::::::::Y:::::::::::::::::::::::::::::::M:::::::::   150
Bm86GAV   82   ::::::::Y:I:::::::::::::::::::::::::::::M::::::::   131

Rm86TX    151  TCLRPDLTCKDLCEKNLLQRDSRCCQGWNTANCSAAPPADSYCSPGSPKG   200
Bm86TICK  151  ::::::::::::::::::::::::::::::::::::::::::::::::::   200
Bm86GAV   132  ::::::::::::::::::::::::::::::::::::::::::::::::::   181

Rm86TX    201  PDGQCKNACRTKEAGFVCKHGCRSTDKAYECTCPSGSTVAEDGITCKSIS   250
Bm86TICK  201  ::::::I::::K:::::::::::::G::::::::::::::::::::::::   250
Bm86GAV   182  ::::::I::::K:::::::::::::G::::::::::::::::::::::::   231

Rm86TX    251  YTVSCTVEQKQTCRPTEDCRVQKGTVLCECPWNQHLVGDTCISDCVDKKC   300
Bm86TICK  251  H:::::A:::::::::::::H:::::::::::::::::::::::::::::   300
Bm86GAV   232  H:::::A:::::::::::::H:::::::::::::::::::::::::::::   281

Rm86TX    301  HEEFMDCGVYMNRQSCYCPWKSRKPGPNVNINECLINEYYYTVSFTPNIS   350
Bm86TICK  301  ::::::::::::::::::::::::::::::::::::::::::::::::::   350
Bm86GAV   282  ::::::::::::::::::::::::::::::::::::::::::::::::::   331

Rm86TX    351  FDSDHCKRYEDRVLEAIRTSIGKEVFKVEILNCTQDIKARLIAEKPLSKY   400
Bm86TICK  351  ::::::W::::::::::::::::::::::::::::::::::::::::::H   400
Bm86GAV   332  ::::::W:::::::::::::::::::::::::::::::::::::::::::   381

Rm86TX    401  VLRKLQACEHPIGEWCMMYPKLLIKKNSATEIEEENLCDSLLKNQEAAYK   450
Bm86TICK  401  ::::::::::::::::::::::::::::::::::::::::::D:::::::   450
Bm86GAV   382  ::::::::::::::::::::::::::::::::::::::::::D:::::::   431

Rm86TX    451  GQNKCVKVDNLFWFQCADGYTTTYEMTRGRLRRSVCKAGVSCNENEQLEC   500
Bm86TICK  451  :::::::::::::::::::::::::::::::::::::::::::::::S::   500
Bm86GAV   432  :::::::::::::::::::::::::::::::::::::::::::::::S::   481

Rm86TX    501  ANKGQICVYENGKANCQCPPDTKPGEIGCIERTTCNPKEIQECQDKKLEC   550
Bm86TICK  501  :D::::F:::::::::::::::::::::::::::::::::::::::::::   550
Bm86GAV   482  :D::::F:::::::::::::::::::::::::::::::::::::::::::   531

Rm86TX    551  VYKNHKAECKCPDDHECSREPAKDSCSEEDNGKCQSSGQRCVMENGNAVC   600
Bm86TICK  551  :::::::::E:::::::Y::::::::::::::::::::::I:::K:::   600
Bm86GAV   532  :::::::::E:::::::Y::::::::::::::::::::::I:::K:::   581

Rm86TX    601  KEKSDATTASTTTTKAKDKDPDPEKSSAAAVSATGLLLLLAATSVTAASL   650
Bm86TICK  601  ::::E::::A:::::::::::::::::::G::::                 650
Bm86GAV   582  ::::E::::A:::::::::::::::::::G::::                 609
```

FIG. 1

(A) Rm86TX Open Reading Frame Sequence (No vector-added sequence)
MRGIALFVAAVSLIVECTAESSICSDFGNEFCRNAECEVVPGAEDDFVCKCPRDNMYFNAAEKQCEYKDT
CKTRECSYGRCVESNPSKGSCVCEASDDLTLQCKIKNDFATDCRNRGGTAKLRTDGFIGATCDCGEWGAM
NKTTRNCVPTTCLRPDLTCKDLCEKNLLQRDSRCCQGWNTANCSAAPPADSYCSPGSPKGPDGQCKNACR
TKEAGFVCKHGCRSTDKAYECTCPSGSTVAEDGITCKSISYTVSCTVEQKQTCRPTEDCRVQKGTVLCEC
PWNQHLVGDTCISDCVDKKCHEEFMDCGVYMNRQSCYCPWKSRKPGPNVNINECLLNEYYYTVSFTPNIS
FDSDHCKRYEDRVLEAIRTSIGKEVFKVEILNCTQDIKARLIAEKPLSKYVLRKLQACEHPIGEWCMMYP
KLLIKKNSATEIEEENLCDSLLKNQEAAYKGQNKCVKVDNLFWFQCADGYTTTYEMTRGRLRRSVCKAGV
SCNENEQLECANKGQICVYENGKANCQCPPDTKPGEIGCIERTTCNPKEIQECQDKKLECVYKNHKAECK
CPDDHECSREPAKDSCSEEDNGKCQSSGQRCVMENGNAVCKEKSDATTASTTTTKAKDKDPDPEKSSAAA
VSATGLLLLLAATSVTAASL (B) Rm86TX ORF in Yeast Pichia Pastoris Vector
MGGIALFVAAVSLIVECTAESSICSDFGNEFCRNAECEVVPGAEDDFVCKCPRDNMYFNAAEKQCEYKDT
CKTRECSYGRCVESNPSKGSCVCEASDDLTLQCKIKNDFATDCRNRGGTAKLRTDGFIGATCDCGEWGAM
NKTTRNCVPTTCLRPDLTCKDLCEKNLLQRDSRCCQGWNTANCSAAPPADSYCSPGSPKGPDGQCKNACR
TKEAGFVCKHGCRSTDKAYECTCPSGSTVAEDGITCKSISYTVSCTVEQKQTCRPTEDCRVQKGTVLCEC
PWNQHLVGDTCISDCVDKKCHEEFMDCGVYMNRQSCYCPWKSRKPGPNVNINECLLNEYYYTVSFTPNIS
FDSDHCKRYEDRVLEAIRTSIGKEVFKVEILNCTQDIKARLIAEKPLSKYVLRKLQACEHPIGEWCMMYP
KLLIKKNSATEIEEENLCDSLLKNQEAAYKGQNKCVKVDNLFWFQCADGYTTTYEMTRGRLRRSVCKAGV
SCNENEQLECANKGQICVYENGKANCQCPPDTKPGEIGCIERTTCNPKEIQECQDKKLECVYKNHKAECK
CPDDHECSREPAKDSCSEEDNGKCQSSGQRCVMENGNAVCKEKSDATTASTTTTKAKDKDPDPEKSSAAA
VSATGLLLLLAATSVTAASLRPPAYVEQKLISEEDLNSAVDHHHHHH*

(C) Rm86TX reading frame
ATGCGTGGCATCGCTTTGTTCGTCGCCGCTGTTTCACTGATTGTAGAGTGCACAGCAGAATCATCCATTT
GCTCTGACTTCGGGAACGAGTTCTGTCGCAACGCTGAATGTGAAGTGGTGCCTGGTGCAGAGGATGATTT
CGTGTGCAAATGTCCGCGAGATAATATGTACTTCAATGCTGCTGAAAAGCAATGCGAATATAAAGATACG
TGCAAGACAAGGGAGTGCAGCTATGGACGTTGCGTTGAAAGTAACCCGAGCAAGGGTAGCTGCGTCTGCG
AAGCATCGGACGATCTAACGCTACAATGCAAAATTAAAAATGACTTCGCAACTGACTGCCGAAACCGAGG
TGGCACTGCTAAGTTGCGCACGGATGGGTTTATTGGCGCAACGTGTGACTGTGGTGAATGGGGTGCGATG
AACAAGACCACACGGAACTGTGTCCCTACCACGTGTCTTCGTCCCGACTTGACCTGCAAAGACCTCTGCG
AGAAAAACCTGCTTCAAAGGGATTCTCGTTGTTGTCAGGGGTGGAACACAGCAAACTGTTCAGCCGCTCC
TCCAGCTGACTCCTATTGCTCTCCTGGGAGCCCCAAAGGACCGGACGGACAGTGTAAAAATGCTTGCAGG
ACGAAAGAAGCTGGGTTTGTCTGCAAGCATGGATGCAGGTCCACCGACAAGGCGTACGAGTGCACGTGCC
CGAGTGGCTCTACCGTCGCCGAAGATGGCATTACCTGCAAAAGTATTTCGTACACAGTCAGCTGCACTGT
TGAGCAAAAACAGACCTGCCGCCCAACCGAAGACTGTCGTGTGCAGAAAGGAACTGTGTTGTGTGAGTGC
CCGTGGAATCAACATCTAGTGGGGACACGTGCATAAGTGATTGCGTCGACAAGAAATGTCACGAAGAAT
TTATGGACTGTGGCGTATATATGAATCGACAAAGCTGCTATTGTCCATGGAAATCAAGGAAGCCGGGCCC
AAATGTCAACATCAATGAATGCCTACTGAATGAGTATTACTACACGGTGTCATTCACCCCGAACATATCT
TTTGATTCTGACCATTGCAAACGGTATGAGGATCGTGTTTTGGAAGCGATACGGACCAGTATCGGAAAAG
AAGTTTTTAAGGTTGAGATACTTAACTGCACGCAGGACATTAAGGCAAGACTCATAGCAGAGAAACCACT
GTCAAAATACGTGCTCAGGAAACTACAAGCATGCGAGCATCCAATCGGCGAATGGTGCATGATGTATCCG
AAGTTGCTGATCAAGAAAAACTCTGCAACAGAAATTGAAGAAGAGAACCTTTGCGACAGTCTGCTCAAGA
ATCAGGAAGCTGCCTACAAAGGTCAAAACAAATGCGTCAAGGTCGACAACCTCTTCTGGTTCCAGTGCGC
TGATGGTTACACAACAACTTACGAGATGACACGAGGTCGCCTACGCCGCTCCGTGTGTAAAGCTGGAGTT
TCTTGCAACGAAAACGAGCAGTTGGAGTGTGCTAACAAAGGTCAAATATGTGTCTACGAAAACGGCAAAG
CGAATTGCCAATGCCCACCAGACACTAAACCAGGGGAGATTGGCTGCATTGAGCGTACCACATGCAACCC
TAAAGAGATACAAGAATGCCAAGACAAGAAGCTCGAGTGCGTTTACAAAAACCATAAAGCAGAATGCAAG
TGTCCTGATGATCACGAGTGTTCTAGGGAGCCTGCCAAAGACTCTTGCAGTGAAGAAGATAATGGTAAAT
GTCAAAGCAGTGGGCAGCGTTGTGTAATGGAAAACGGAAATGCTGTTTGCAAAGAGAAGTCTGATGCAAC
AACAGCTTCGACTACAACAACGAAAGCGAAAGACAAGGATCCAGATCCTGAAAAGTCAAGTGCTGCAGCA
GTATCAGCTACTGGGCTCTTGTTACTGCTCGCAGCTACTTCAGTCACCGCAGCATCGTTGTAATGAAGAT
GTCCAACTTGAATACGGAACAGCTTGAAAATGTATATATACATCACGCTTACATCGAACACC

FIG. 2

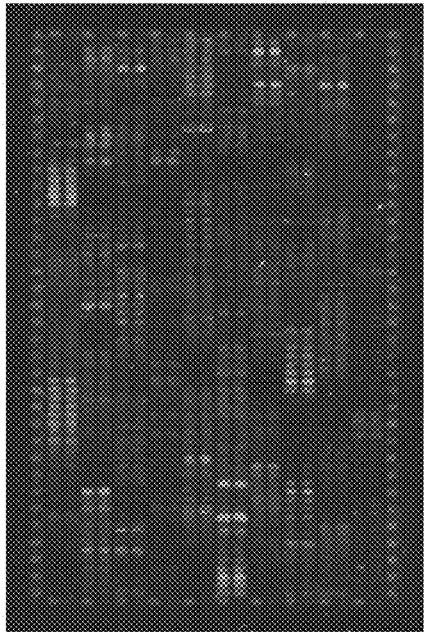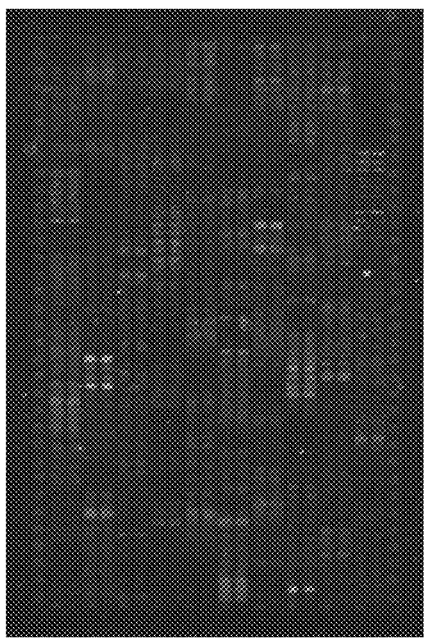
FIG. 6

SEQUENCE LISTING

<160> NUMBER OF SEQ ID NOS: 7

<210> SEQ ID NO 1
<211> LENGTH: 650
<212> TYPE: PRT
<213> ORGANISM: Rhipicephalus microplus

<400> SEQUENCE: 1

```
Met Arg Gly Ile Ala Leu Phe Val Ala Val Ser Leu Ile Val Glu
1               5                   10                  15

Cys Thr Ala Glu Ser Ser Ile Cys Ser Asp Phe Gly Asn Glu Phe Cys
            20                  25                  30

Arg Asn Ala Glu Cys Glu Val Val Pro Gly Ala Glu Asp Asp Phe Val
        35                  40                  45

Cys Lys Cys Pro Arg Asp Asn Met Tyr Phe Asn Ala Ala Glu Lys Gln
50                  55                  60

Cys Glu Tyr Lys Asp Thr Cys Lys Thr Arg Glu Cys Ser Tyr Gly Arg
65                  70                  75                  80

Cys Val Glu Ser Asn Pro Ser Lys Gly Ser Cys Val Cys Glu Ala Ser
                85                  90                  95

Asp Asp Leu Thr Leu Gln Cys Lys Ile Lys Asn Asp Phe Ala Thr Asp
            100                 105                 110

Cys Arg Asn Arg Gly Gly Thr Ala Lys Leu Arg Thr Asp Gly Phe Ile
        115                 120                 125

Gly Ala Thr Cys Asp Cys Gly Glu Trp Gly Ala Met Asn Lys Thr Thr
    130                 135                 140

Arg Asn Cys Val Pro Thr Thr Cys Leu Arg Pro Asp Leu Thr Cys Lys
145                 150                 155                 160

Asp Leu Cys Glu Lys Asn Leu Leu Gln Arg Asp Ser Arg Cys Cys Gln
                165                 170                 175

Gly Trp Asn Thr Ala Asn Cys Ser Ala Ala Pro Pro Ala Asp Ser Tyr
            180                 185                 190

Cys Ser Pro Gly Ser Pro Lys Gly Pro Asp Gly Gln Cys Lys Asn Ala
        195                 200                 205

Cys Arg Thr Lys Glu Ala Gly Phe Val Cys Lys His Gly Cys Arg Ser
    210                 215                 220

Thr Asp Lys Ala Tyr Glu Cys Thr Cys Pro Ser Gly Ser Thr Val Ala
225                 230                 235                 240

Glu Asp Gly Ile Thr Cys Lys Ser Ile Ser Tyr Thr Val Ser Cys Thr
                245                 250                 255

Val Glu Gln Lys Gln Thr Cys Arg Pro Thr Glu Asp Cys Arg Val Gln
            260                 265                 270

Lys Gly Thr Val Leu Cys Glu Cys Pro Trp Asn Gln His Leu Val Gly
        275                 280                 285

Asp Thr Cys Ile Ser Asp Cys Val Asp Lys Lys Cys His Glu Glu Phe
    290                 295                 300

Met Asp Cys Gly Val Tyr Met Asn Arg Gln Ser Cys Tyr Cys Pro Trp
305                 310                 315                 320

Lys Ser Arg Lys Pro Gly Pro Asn Val Asn Ile Asn Glu Cys Leu Leu
                325                 330                 335

Asn Glu Tyr Tyr Tyr Thr Val Ser Phe Thr Pro Asn Ile Ser Phe Asp
            340                 345                 350

Ser Asp His Cys Lys Arg Tyr Glu Asp Arg Val Leu Glu Ala Ile Arg
        355                 360                 365
```

```
Thr Ser Ile Gly Lys Glu Val Phe Lys Val Glu Ile Leu Asn Cys Thr
        370                 375                 380

Gln Asp Ile Lys Ala Arg Leu Ile Ala Glu Lys Pro Leu Ser Lys Tyr
385                 390                 395                 400

Val Leu Arg Lys Leu Gln Ala Cys Glu His Pro Ile Gly Glu Trp Cys
                405                 410                 415

Met Met Tyr Pro Lys Leu Leu Ile Lys Lys Asn Ser Ala Thr Glu Ile
            420                 425                 430

Glu Glu Glu Asn Leu Cys Asp Ser Leu Leu Lys Asn Gln Glu Ala Ala
        435                 440                 445

Tyr Lys Gly Gln Asn Lys Cys Val Lys Val Asp Asn Leu Phe Trp Phe
    450                 455                 460

Gln Cys Ala Asp Gly Tyr Thr Thr Tyr Glu Met Thr Arg Gly Arg
465                 470                 475                 480

Leu Arg Arg Ser Val Cys Lys Ala Gly Val Ser Cys Asn Glu Asn Glu
                485                 490                 495

Gln Leu Glu Cys Ala Asn Lys Gly Gln Ile Cys Val Tyr Glu Asn Gly
            500                 505                 510

Lys Ala Asn Cys Gln Cys Pro Asp Thr Lys Pro Gly Glu Ile Gly
        515                 520                 525

Cys Ile Glu Arg Thr Thr Cys Asn Pro Lys Glu Ile Gln Glu Cys Gln
    530                 535                 540

Asp Lys Lys Leu Glu Cys Val Tyr Lys Asn His Lys Ala Glu Cys Lys
545                 550                 555                 560

Cys Pro Asp Asp His Glu Cys Ser Arg Glu Pro Ala Lys Asp Ser Cys
                565                 570                 575

Ser Glu Glu Asp Asn Gly Lys Cys Gln Ser Ser Gly Gln Arg Cys Val
            580                 585                 590

Met Glu Asn Gly Asn Ala Val Cys Lys Glu Lys Ser Asp Ala Thr Thr
        595                 600                 605

Ala Ser Thr Thr Thr Lys Ala Lys Asp Lys Asp Pro Asp Pro Glu
    610                 615                 620

Lys Ser Ala Ala Ala Val Ser Ala Thr Gly Leu Leu Leu Leu
625                 630                 635                 640

Ala Ala Thr Ser Val Thr Ala Ala Ser Leu
                645                 650

<210> SEQ ID NO 2
<211> LENGTH: 677
<212> TYPE: PRT
<213> ORGANISM: Rhipicephalus microplus

<400> SEQUENCE: 2

Met Gly Gly Ile Ala Leu Phe Val Ala Ala Val Ser Leu Ile Val Glu
1               5                   10                  15

Cys Thr Ala Glu Ser Ser Ile Cys Ser Asp Phe Gly Asn Glu Phe Cys
            20                  25                  30

Arg Asn Ala Glu Cys Glu Val Val Pro Gly Ala Glu Asp Asp Phe Val
        35                  40                  45

Cys Lys Cys Pro Arg Asp Asn Met Tyr Phe Asn Ala Ala Glu Lys Gln
    50                  55                  60

Cys Glu Tyr Lys Asp Thr Cys Lys Thr Arg Glu Cys Ser Tyr Gly Arg
65                  70                  75                  80

Cys Val Glu Ser Asn Pro Ser Lys Gly Ser Cys Val Cys Glu Ala Ser
                85                  90                  95
```

```
Asp Asp Leu Thr Leu Gln Cys Lys Ile Lys Asn Asp Phe Ala Thr Asp
            100                 105                 110

Cys Arg Asn Arg Gly Gly Thr Ala Lys Leu Arg Thr Asp Gly Phe Ile
        115                 120                 125

Gly Ala Thr Cys Asp Cys Gly Glu Trp Gly Ala Met Asn Lys Thr Thr
130                 135                 140

Arg Asn Cys Val Pro Thr Thr Cys Leu Arg Pro Asp Leu Thr Cys Lys
145                 150                 155                 160

Asp Leu Cys Glu Lys Asn Leu Leu Gln Arg Asp Ser Arg Cys Cys Gln
                165                 170                 175

Gly Trp Asn Thr Ala Asn Cys Ser Ala Ala Pro Pro Ala Asp Ser Tyr
            180                 185                 190

Cys Ser Pro Gly Ser Pro Lys Gly Pro Asp Gly Gln Cys Lys Asn Ala
        195                 200                 205

Cys Arg Thr Lys Glu Ala Gly Phe Val Cys Lys His Gly Cys Arg Ser
        210                 215                 220

Thr Asp Lys Ala Tyr Glu Cys Thr Cys Pro Ser Gly Ser Thr Val Ala
225                 230                 235                 240

Glu Asp Gly Ile Thr Cys Lys Ser Ile Ser Tyr Thr Val Ser Cys Thr
                245                 250                 255

Val Glu Gln Lys Gln Thr Cys Arg Pro Thr Glu Asp Cys Arg Val Gln
            260                 265                 270

Lys Gly Thr Val Leu Cys Glu Cys Pro Trp Asn Gln His Leu Val Gly
        275                 280                 285

Asp Thr Cys Ile Ser Asp Cys Val Asp Lys Lys Cys His Glu Glu Phe
        290                 295                 300

Met Asp Cys Gly Val Tyr Met Asn Arg Gln Ser Cys Tyr Cys Pro Trp
305                 310                 315                 320

Lys Ser Arg Lys Pro Gly Pro Asn Val Asn Ile Asn Glu Cys Leu Leu
                325                 330                 335

Asn Glu Tyr Tyr Tyr Thr Val Ser Phe Thr Pro Asn Ile Ser Phe Asp
            340                 345                 350

Ser Asp His Cys Lys Arg Tyr Glu Asp Arg Val Leu Glu Ala Ile Arg
        355                 360                 365

Thr Ser Ile Gly Lys Glu Val Phe Lys Val Glu Ile Leu Asn Cys Thr
        370                 375                 380

Gln Asp Ile Lys Ala Arg Leu Ile Ala Glu Lys Pro Leu Ser Lys Tyr
385                 390                 395                 400

Val Leu Arg Lys Leu Gln Ala Cys Glu His Pro Ile Gly Glu Trp Cys
                405                 410                 415

Met Met Tyr Pro Lys Leu Leu Ile Lys Lys Asn Ser Ala Thr Glu Ile
            420                 425                 430

Glu Glu Glu Asn Leu Cys Asp Ser Leu Leu Lys Asn Gln Glu Ala Ala
        435                 440                 445

Tyr Lys Gly Gln Asn Lys Cys Val Lys Val Asp Asn Leu Phe Trp Phe
        450                 455                 460

Gln Cys Ala Asp Gly Tyr Thr Thr Thr Tyr Glu Met Thr Arg Gly Arg
465                 470                 475                 480

Leu Arg Arg Ser Val Cys Lys Ala Gly Val Ser Cys Asn Glu Asn Glu
                485                 490                 495

Gln Leu Glu Cys Ala Asn Lys Gly Gln Ile Cys Val Tyr Glu Asn Gly
            500                 505                 510
```

```
Lys Ala Asn Cys Gln Cys Pro Pro Asp Thr Lys Pro Gly Glu Ile Gly
            515                 520                 525
Cys Ile Glu Arg Thr Thr Cys Asn Pro Lys Glu Ile Gln Glu Cys Gln
        530                 535                 540
Asp Lys Lys Leu Glu Cys Val Tyr Lys Asn His Lys Ala Glu Cys Lys
545                 550                 555                 560
Cys Pro Asp Asp His Glu Cys Ser Arg Glu Pro Ala Lys Asp Ser Cys
                565                 570                 575
Ser Glu Glu Asp Asn Gly Lys Cys Gln Ser Ser Gly Gln Arg Cys Val
            580                 585                 590
Met Glu Asn Gly Asn Ala Val Cys Lys Glu Lys Ser Asp Ala Thr Thr
        595                 600                 605
Ala Ser Thr Thr Thr Thr Lys Ala Lys Asp Lys Asp Pro Asp Pro Glu
    610                 615                 620
Lys Ser Ala Ala Ala Val Ser Ala Thr Gly Leu Leu Leu Leu Leu Leu
625                 630                 635                 640
Ala Ala Thr Ser Val Thr Ala Ala Ser Leu Arg Pro Pro Ala Tyr Val
                645                 650                 655
Glu Gln Lys Leu Ile Ser Glu Glu Asp Leu Asn Ser Ala Val Asp His
            660                 665                 670
His His His His His
        675

<210> SEQ ID NO 3
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 3
atgcgtggca tcgctttgtt                                              20

<210> SEQ ID NO 4
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 4
ggtgttcgat gtaagcgtga tg                                           22

<210> SEQ ID NO 5
<211> LENGTH: 27
<212> TYPE: PRT
<213> ORGANISM: Artificial Sequence
<220> FEATURE:
<223> OTHER INFORMATION: Chemically Synthesized

<400> SEQUENCE: 5

Arg Pro Pro Ala Tyr Val Glu Gln Lys Leu Ile Ser Glu Glu Asp Leu
1               5                   10                  15
Asn Ser Ala Val Asp His His His His His
            20                  25

<210> SEQ ID NO 6
<211> LENGTH: 10
<212> TYPE: PRT
<213> ORGANISM: Artificial Sequence
<220> FEATURE:
```

```
<223> OTHER INFORMATION: Chemically Synthesized

<400> SEQUENCE: 6

Asp Tyr Lys Asp Asp Asp Lys Gly Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 7

Tyr Pro Tyr Asp Val Pro Asp Tyr Ala Gly
1               5                   10
```

VACCINATION WITH ANTI-TICK ANTIGENS TO CONTROL MULTIPLE TICK SPECIES AND DISEASE TRANSMISSION IN WHITE-TAILED DEER AND OTHER HOST ANIMALS

REFERENCE TO RELATED APPLICATIONS

This application claims the benefit of U.S. Provisional Application No. 62/398,706 filed Sep. 23, 2016, which is incorporated herein by reference in its entirety.

BACKGROUND

This invention relates to methods to control and prevent tick infestations in immunized non-bovine animals, including deer, which further protects the animals against the transmission of tick-borne pathogens.

Ticks pose a significant risk to the health and welfare of warm-blooded animals as the vectors for a large number of pathogenic agents, including protozoan parasites, viruses and bacteria. For instance, babesiosis is a devastating infectious disease that causes great economic loss to the cattle industry and is transmitted by cattle ticks, including *Rhipicephalus microplus*. White-tailed deer are capable of sustaining *Rhipicephalus* spp. tick populations in the presence or absence of cattle, and evidence has shown the role of deer in tick dispersal and tick population maintenance. The emergence of some unique strains of *Babesia* in humans in Tennessee points to a zoonotic transmission of babesiosis to humans, stressing the importance of tick control in wildlife and domestic animals Ticks are also carriers of a number of other common tick-borne infectious disease agents such as tick-borne encephalitis virus, Crimean-Congo hemorrhagic fever virus, Nairobi sheep virus, *Borrelia burgdorferi* (the agent of Lyme disease), and *Theileria parva* (the agent of East Coast fever), as well as other injurious effects that have major impacts in human and veterinary medicine.

The white-tailed deer is the known keystone host for several species of tick, including *Ixodes scapularis* (commonly known as the deer tick) and *Amblyomma americanum* (commonly known as the lone star tick). Both of these ticks act as disease vectors, spreading for example Lyme disease, and both infest white-tailed deer populations in the United States. Studies have shown that white-tailed deer even act as disease reservoirs for the pathogens spread by these ticks.

As a result of the spread of pesticide-resistant strains of these and other ticks and flies, there is a growing need to develop improved tools for their control. Attempts have been made to use immunological means of control through vaccine technology. Some success has been met in identifying certain protective antigens of arthropod parasites as being potential vaccine candidates, but only a few have as yet come to commercial fruition. Despite these developments, there is nonetheless a continuing need for arthropod parasite vaccines and in particular for a vaccine which may be used against ticks, including the brown dog tick.

All of the references cited herein, including U.S. Patents and U.S. Patent Application Publications, are incorporated by reference in their entirety. Also incorporated by reference in their entirety are the following references:

SUMMARY

Compositions of either the Rm86Texas protein from a Texas outbreak strain of the southern cattle fever tick, *Rhipicephalus microplus*, or a nucleic acid construct incorporating a nucleic acid sequence encoding this Rm86Texas protein, are effective for eliciting a protective immune response in non-bovine animals. The Rm86Texas protein is immunogenic and can be administered as a protein vaccine, or in the alternative, the nucleic acid construct can be utilized as a DNA vaccine. Induction of the immune response significantly reduces or eliminates the infestation of treated, non-bovine animals with ticks. Moreover, as ticks are vectors of a variety of pathogens, the reduction in the incidence of tick infestation afforded by the vaccines may concurrently reduce the incidence of diseases caused by these pathogens in susceptible animals.

Accordingly, it is an object of this invention to provide protective vaccines against ticks, including both *R. microplus* and other ticks, in non-bovine animals.

Another object of the invention is to provide protective vaccines that control and prevent infestations with ticks of different species than the southern cattle fever tick, and in animals different from bovine.

A further object of the invention is to provide protective vaccines against infestation and diseases transmitted by *Ixodes scapularis* and *Amblyomma americanum* in animals.

Yet another object of the invention is to provide protective vaccines against ticks in companion animals, including deer, horses, and domestic dogs and cats.

Still another object of the invention is to provide protective vaccines that control and prevent animal infestations with ticks, and thereby reduce or eliminate the incidence of diseases caused by pathogenic agents carried by the ticks.

Other objects and advantages of this invention will become readily apparent from the ensuing description.

BRIEF DESCRIPTION OF THE FIGURES

Advantages of embodiments of the present invention will be apparent from the following detailed description of the exemplary embodiments. The following detailed description should be considered in conjunction with the accompanying figures in which:

FIG. 1 shows the amino acid sequence of Rm86Texas compared to BM86, as developed in Australia (Bm86TICK) and Cuba (Bm86GAV).

FIG. 2 shows the sequence of Rm86Texas, as used in an exemplary embodiment of the present invention.

FIG. 6 shows peptide microarrays following incubation with pre- and post-vaccination serum.

SEQUENCE LISTING

Figure 3:
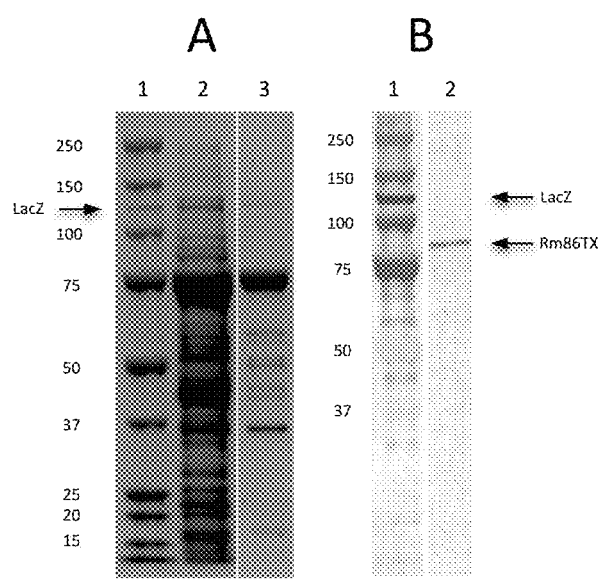
FIG. 3 shows Western blots of the purification of Rm86Texas as expressed in *Pichia pastoris*.

The Sequence Listing submitted via EFS-Web as an ASCII compliant text file format (.txt) filed Nov. 15, 2018, named "Sequence_Listing-016315_CORRECTED_11-15-2018" (created Nov. 15, 2018, 13 kb), is hereby incorporated herein by reference in its entirety. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

SEQUENCES

The invention can be more fully understood from the following detailed description and the accompanying sequence descriptions, which form a part of this application.

SEQ ID NO: 1
MRGIALFVAAVSLIVECTAESSICSDFGNEFCRNAECEVVPGAED
DFVCKCPRDNMYFNAAEKQCEYKDTCKTRECSYGRCVESNPSKGSCVCE
ASDDLTLQCKIKNDFATDCRNRGGTAKLRTDGFIGATCDCGEWGAMNKT
TRNCVPTTCLRPDLTCKDLCEKNLLQRDSRCCQGWNTANCSAAPPADSY
CSPGSPKGPDGQCKNACRTKEAGFVCKHGCRSTDKAYECTCPSGSTVAE
DGITCKSISYTVSCTVEQKQTCRPTEDCRVQKGTVLCECPWNQHLVGDT
CISDCVDKKCHEEFMDCGVYMNRQSCYCPWKSRKPGPNVNINECLLNEY
YYTVSFTPNISFDSDHCKRYEDRVLEAIRTSIGKEVFKVEILNCTQDIK
ARLIAEKPLSKYVLRKLQACEHPIGEWCMMYPKLLIKKNSATEIEEENL
CDSLLKNQEAAYKGQNKCVKVDNLFWFQCADGYTTTYEMTRGRLRRSVC
KAGVSCNENEQLECANKGQICVYENGKANCQCPPDTKPGEIGCIERTTC
NPKEIQECQDKKLECVYKNHKAECKCPDDHECSREPAKDSCSEEDNGKC
QSSGQRCVMENGNAVCKEKSDATTASTTTTKAKDKDPDPEKSSAAAVSA
TGLLLLLAATSVTAASL comprises the Rm86Texas protein open reading frame.

SEQ ID NO: 2
MGGIALFVAAVSLIVECTAESSICSDFGNEFCRNAECEVVPGAED
DFVCKCPRDNMYFNAAEKQCEYKDTCKTRECSYGRCVESNPSKGSCVCE
ASDDLTLQCKIKNDFATDCRNRGGTAKLRTDGFIGATCDCGEWGAMNKT
TRNCVPTTCLRPDLTCKDLCEKNLLQRDSRCCQGWNTANCSAAPPADSY
CSPGSPKGPDGQCKNACRTKEAGFVCKHGCRSTDKAYECTCPSGSTVAE
DGITCKSISYTVSCTVEQKQTCRPTEDCRVQKGTVLCECPWNQHLVGDT
CISDCVDKKCHEEFMDCGVYMNRQSCYCPWKSRKPGPNVNINECLLNEY
YYTVSFTPNISFDSDHCKRYEDRVLEAIRTSIGKEVFKVEILNCTQDIK
ARLIAEKPLSKYVLRKLQACEHPIGEWCMMYPKLLIKKNSATEIEEENL
CDSLLKNQEAAYKGQNKCVKVDNLFWFQCADGYTTTYEMTRGRLRRSVC
KAGVSCNENEQLECANKGQICVYENGKANCQCPPDTKPGEIGCIERTTC
NPKEIQECQDKKLECVYKNHKAECKCPDDHECSREPAKDSCSEEDNGKC
QSSGQRCVMENGNAVCKEKSDATTASTTTTKAKDKDPDPEKSSAAAVSA
TGLLLLLAATSVTAASLRPPAYVEQKLISEEDLNSAVDHHHHHH is the Rm86Tex as protein optimized for expression in a yeast vector.

SEQ ID NO: 3 ATGCGTGGCATCGCTTTGTT is a Bm86 PCR forward primer.

SEQ ID NO: 4 GGTGTTCGATGTAAGCGTGATG is a Bm86 PCR reverse primer.

SEQ ID NO: 5 RPPAYVEQKLISEEDLNSAVDHHH-HHH is a c-myc epitope and a 6x-histidine tag used in the Rm86Texas protein optimized for expression in yeast.

SEQ ID NO: 6 DYKDDDDKGG is FLAG, a control epitope tag peptide.

SEQ ID NO: 7 YPYDVPDYAG is the control epitope peptide for human influenza hemaglutinin A.

DEFINITIONS

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms which may be used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

Complement or Complementary Sequence. The product of complementary base pairing in which purines bond with pyrimidines, as it occurs in the two polynucleotide chains of DNA (adenine with thymine, guanine with cytosine) and between DNA and messenger RNA nucleotides during transcription.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, prokaryotic sequences and cDNA from eukaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Effective Amount. Such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation. Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase, which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in the correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism, a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant".

Polypeptide. A linear series of amino acids connected one to the other by peptide bonds between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Start Codon. Also called the initiation codon, is the first mRNA triplet to be translated during protein or peptide synthesis and immediately precedes the structural gene being translated. The start codon is usually AUG, but may sometimes also be GUG.

Stringent Hybridization Conditions. The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will differ in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. It is also understood that due to the advances in DNA PCR and sequencing approaches that issues of gene identity and homology may be determined by sequence based rather than hybridization approaches.

Structural Gene. A DNA sequence which encodes through its template or messenger RNA (mRNA) a sequence of amino acids characteristic of a specific polypeptide.

Substantially Pure. The condition of a compound, such as a protein or a nucleotide, being cell free or being separated from other components that would interfere with or have a substantial qualitative effect on the activity of the compound or on a substrate on which the compound acts.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In prokaryotes and some fungi, for example, the exogenous DNA may be maintained on an episomal element such as a plasmid. With respect to most eukaryotic cells, a stably transformed cell is one in which the exogenous DNA has been integrated into a chromosome so that it is inherited by daughter cells through chromosome replication. This stability is demonstrated by the ability of the eukaryotic cell to establish cell lines or clones comprised of a population of daughter cells containing the exogenous DNA.

Transcription. The process of producing mRNA from a structural gene.

Translation. The process of producing a polypeptide from mRNA.

Vaccine. Vaccine is defined herein in its broad sense to refer to any type of biological agent in an administrable form capable of stimulating a protective immune response in an animal inoculated with the vaccine. For purposes of this invention, the vaccine may comprise either one or more of the immunogenic (antigenic) proteins or nucleic acid constructs encoding these proteins.

Further, other compounds may be added to the composition provided they do not substantially interfere with the intended activity and efficacy of the composition; whether or not a compound interferes with activity and/or efficacy can be determined, for example, by the procedures utilized below.

The amounts, percentages, and ranges disclosed herein are not meant to be limiting, and increments between the recited amounts, percentages, and ranges are specifically envisioned as part of the invention.

DETAILED DESCRIPTION

At least one of the immunogenic proteins which is utilized herein is the recombinant antigen Rm86Texas, derived from the Bm86 sequence variant of a Texas outbreak population of *R. microplus*, in white-tailed deer. The Bm86 protein is located on the microvilli of the tick gut digestive cells. The recombinant antigen was formulated with an oil-based adjuvant for use in a vaccine trial to compare the immune response of white-tailed deer immunized with the Rm86Texas plus adjuvant to other white-tailed deer injected with adjuvant alone.

The Rm86Texas protein fragment of the cattle tick, *R. microplus*, has been isolated, substantially free from other proteins or cell components which are normally present in the cells of the tick, such that the protein is the only significant immunogen in the sample and may be used effectively as a vaccine. Moreover, the protein has been produced in recombinant form as described herein below. The term "isolated" encompasses not only proteins which have been recovered from naturally occurring cells, but also recombinant proteins and synthesized proteins. The Rm86Texas protein fragments, including recombinants, are immunogenic, effective for eliciting a protective immune response against ticks including the cattle tick and others, which response is mediated by humoral, i.e., antibodies, and/or cellular processes.

It is envisioned that the Rm86Texas protein may be synthesized by any suitable method well known to those skilled in the art of peptide synthesis, such as exclusively solid-phase techniques, partial solid-phase techniques, fragment condensation, or classical solution addition. For example, without being limited thereto, suitable solution phase synthesis methods are described by Finn and Hoffman [in "Proteins," Vol. 2, 3rd Ed., H. Neurath and R. L. Hill (eds.), Academic Press, New York, pp. 105-253 (1976)], while solid phase synthesis methods are described by Barany and Merrifield [in "The Peptides," Vol. 2, E. Gross and J. Meienhofer (eds.), Academic Press, New York, pp. 3-284 (1979)], and stepwise solid phase synthesis methods are described by Merrifield [in J. Am. Chem. Soc. 85: 2149-2154 (1963)], the contents of each of which are incorporated herein by reference. However, the protein is preferably produced by recombinant DNA techniques which are particularly suitable for large-scale use. Without being limited thereto, nucleotide sequences encoding the protein which are preferred for use in recombinant DNA techniques are described in detail below. The synthetic protein may be obtained by transforming a microorganism using an expression vector including a promoter or operator, or both, together with the Rm86Texas structural gene and causing such transformed microorganisms to express the protein.

The gene encoding the Rm86Texas protein has also been isolated and sequenced, as described below. As used herein, isolated nucleic acid sequences refer to sequences which have been substantially separated from other nucleic acids or cell components which are normally present in the cells of the tick, such that the Rm86Texas encoding sequences are the only significant sequences in the sample that can be used to express or produce the protein in a host cell as described below. The term encompasses not only nucleic acid sequences which have been recovered from naturally occurring cells, but also recombinant or cloned nucleic acid sequences, and synthesized nucleic acid sequences. The nucleic acid sequences may be recovered from cells of *R. microplus*, for example, by constructing a genomic DNA or cDNA library and screening for the Rm86Texas protein nucleic acid using the disclosed sequences as probes. However, in a preferred embodiment, the sequences are synthesized using techniques established in the art for automated DNA synthesis or amplification. As used herein, the nucleic acid sequences of the Rm86Texas protein encompass either or both of the coding strand or its complement.

As noted herein, the amino acid sequence of the Rm86Texas protein may be modified to assist cloning in the selected vector, and may further include optional, additional terminal amino acid sequences from the vector (not of tick origin). Thus, the nucleic acid sequence may be modified to reflect these changes.

In addition, because of the degeneracy of the genetic code, there exists a finite set of nucleotide sequences which can code for a given amino acid sequence. Consequently, nucleic acids may be identical in sequence to the sequence which is naturally occurring or they may include alternative codons which encode the same amino acid as that which is found in the naturally occurring sequence. Furthermore, nucleic acids may include codons which represent conservative substitutions of amino acids as are well known in the art. Moreover, because of the degeneracy of the genetic code, different species can preferentially use different codons to code for the same amino acid and significant differences in tRNA abundance can exist. Translation of recombinant proteins can often be enhanced by optimizing codon usage to the preferred codons used by the expression species. For example, in the yeast *P. pastoris* the amino acid arginine is encoded by the nucleotide triplet of AGA approximately 10 times more frequently than by the nucleotide triplet of CGG. Substitution of CGG triplets with AGA in a *R. microplus* protein coding region used in a recombinant *P. pastoris* expression system would be expected to enhance recombinant protein expression levels. It is understood that all such equivalent sequences are operable variants of the disclosed sequences, since all give rise to the same Rm86Texas protein (i.e., the same amino acid sequence) during in vivo transcription and translation, and are hence encompassed herein. Without being limited thereto, an example of a codon-optimized sequence which would be suitable for enhancing translation of the Rm86Texas protein fragment in *P. pastoris* are shown in FIG. 2(B). The sequence of FIG. 2(B), known as SEQ ID NO: 2 corresponds to the sequence of FIG. 2(A), known as SEQ ID NO: 1, which has been optimized to enhance translation in *P. pastoris*. DNA sequences which contain significant sequence similarity to the coding regions of the nucleotide sequence of SEQ ID NO: 2 are also encompassed by the invention. As defined herein, two DNA sequences contain significant sequence similarity when at least 85% (preferably at least 90% and most preferably 95%) of the nucleotides match over the defined length of the sequence. Sequences that are significantly similar can be identified in a Southern hybridization experiment under stringent hybridization conditions as is known in the art.

Any one or combinations of the isolated cDNA nucleic acid sequences encoding the Rm86Texas protein may be cloned into any suitable vector for subsequent use as either a DNA vaccine or for the production of recombinant Rm86Texas protein. For use as a DNA vaccine, the nucleic acid constructs comprising the nucleic acid sequences encoding the Rm86Texas protein are administered to a subject animal such that the protein is expressed in vivo within the cells of the vaccinated animal. Similarly, where the object is the production of recombinant protein, the nucleic acid constructs are used for the transformation of a microorganism and causing such transformed microorganism to express the protein in vitro.

A variety of vectors are suitable for use herein, and are selected to be operable as cloning vectors or expression vectors in the selected host cell, although expression vectors are preferred. Numerous vectors are known to practitioners skilled in the art, and selection of an appropriate vector and host cell is a matter of choice. The vectors may, for example, be bacteriophage, plasmids (including linearized or circular plasmids), viruses or hybrids thereof, such as those described in Ausubel et al. (Current Protocols in Molecular Biology, John Wiley & Sons, Inc, 1995), the contents of which are herein incorporated by reference. Further, the vectors may be non-fusion vectors (i.e., those producing the proteins of the invention not fused to any heterologous polypeptide), or alternatively, fusion vectors (i.e., those producing the proteins fused to a vector encoded polypeptide). The fusion proteins would of course vary with the particular vector chosen. In accordance with a preferred embodiment, and particularly for applications as DNA vaccines, the vectors are eukaryotic expression vectors, most preferably plasmids. Particularly preferred plasmids for use herein include plasmids commercially available from Invitrogen Inc., Carlsbad, Calif. for both the DNA vaccine and recombinant protein vaccine protocols. The pcDNA 4/myc 5.1 kb vectors are designed for overproduction of recombinant proteins in mammalian cells. This plasmid contains a human cytomegalovirus immediate-early (CMV) promoter for high-level expression, a c-myc epitope and 6×His metal-binding peptide tag for facilitating protein purification and verification, and a Zeocin antibiotic resistance marker gene coding region for selection purposes. The preferred plasmids used to produce recombinant protein may be the pPICZ and pPICZα from Invitrogen Inc. Both plasmids contain the AOX1 gene promoter for methanol-inducible high-level expression in *Pichia pastoris*, a c-myc epitope and 6×His metal-binding peptide tag for facilitating protein purification and verification, and a Zeocin antibiotic resistance marker gene coding region for selection purposes. The pPICZα also contains a native *Saccharomyces cerevisiae* α-factor secretion signal.

Regardless of the specific vector utilized, various sites may be selected for insertion of the isolated nucleotide sequences. These sites are usually designated by the restriction enzyme or endonuclease that cuts them.

The particular site chosen for insertion of the selected nucleotide sequences into the vector to form a recombinant vector is determined by a variety of factors. These include size and structure of the protein to be expressed, susceptibility of the desired protein to enzymatic degradation by the host cell components and contamination by its proteins, expression characteristics such as the location of start and stop codons, and other factors recognized by those skilled in the art. None of these factors alone absolutely controls the choice of insertion site for a particular polypeptide. Rather, the site chosen reflects a balance of these factors, and not all sites may be equally effective for a given protein.

The nucleotide sequences comprising the Rm86Texas protein encoding gene may be inserted into the desired vector by known techniques. If, however, the vector is to serve as an expression vector, the vector should have a promoter effective for expression in the selected host cell, and the DNA sequences should be inserted in the vector downstream of the promoter and operationally associated therewith (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). Preferably, the vector should be selected to provide a region which codes for a ribosomal binding site recognized by the ribosomes of the host cell into which the vector is to be inserted. The vector should contain a terminator with necessary 3' untranslated sequences for RNA termination, stability, and/or poly(A) tail addition (if eukaryotic). Alternatively, any or all of the above control sequences may be ligated to the coding sequence prior to insertion into the vector.

For use in animal vaccinations, the isolated Rm86Texas protein, or the nucleic acid constructs comprising the nucleic acid sequences encoding this protein, will typically be formulated in conjunction with a suitable pharmaceutically acceptable carrier or diluent as is known in the art, including, but not limited to, physiological saline, mineral oil, vegetable oils, aqueous carboxymethyl cellulose or polyvinylpyrrolidone. The skilled practitioner will recognize that such carriers should of course be compatible with the protein or nucleic acid constructs. Because Rm86Texas may precipitate in the presence of aqueous buffers such as Phosphate-Buffered Saline (PBS), in a preferred embodiment the Rm86Texas is stored in a non-polar solvent or oil. A variety of non-polar solvents are suitable for use herein. The concentration and amount of the protein or nucleic acid constructs in the final composition may vary depending upon the desired use and type of response needed, and the host animal. In any event, the protein or nucleic acid constructs should be provided in an amount effective to induce the preferred response as determined by routine testing.

Appropriate adjuvants as known in the art may also be included in the formulation. As described herein, adjuvants include agents (a compound or combination of compounds) capable of enhancing either or both of a humoral (antibody) immunity response or a cell-mediated immunity response in the treated animal against the target tick. Without being limited thereto, suitable adjuvants include but are not limited to one or more of mineral oil, vegetable oils, aluminum salts such as alum, water-in-oil adjuvants such as Freund's incomplete adjuvant, oil-in-water emulsions such as MF59 (Novartis, Switzerland), liposomes, virosomes, microparticles or nanoparticles or beads of biocompatible matrix materials such as (although not limited to) agar or polyacrylate, saponin-based adjuvants (such as QA-21 or QS-21 marketed by Antigenics, Lexington, Mass.), toll-like receptor (TLR) agonists such as 3-O-desacyl-4'-monophosphoryl lipid A (MPL) and immunostimulatory sequences (ISS) of microbial DNA, imidazoquinolines, immune stimulating complexes (ISCOMs and ISCOMATRIXs), and other agents such as described by Leroux-Roels (2010. Vaccine. 285: C25-C36, the contents of which are incorporated by reference herein). In accordance with an optional embodiment, other known immunogenic agents used in conventional vaccines for the animal of interest may also be included in the formulation. For example, additional immunogenic agents may be an attenuated or inactivated form of a pathogen, or subunits thereof. Without being limited thereto, these pathogens include, for example, one or more of the rabies virus, *Borrelia burgdorferi*, canine distemper virus, canine parvovirus, canine adenovirus, canine corona virus, canine herpesvirus, *Giardia* spp., *Leptospira interrogans, Babesia canis, Hepatozoon canis, Dipylidium caninum, Isospora* spp, and other proteins of *R. microplus*.

The immunogenic Rm86Texas protein or the nucleic acid constructs comprising the nucleic acid sequences encoding this protein may be administered in an amount effective to reduce or eliminate the incidence of infestation of the treated animal with a specific target tick. As noted hereinabove, the administration of the Rm86Texas protein, or the nucleic acid constructs comprising the nucleic acid sequences encoding this protein (such that the nucleic acid sequences are expressed and the encoded protein is produced in vivo in the cells of the vaccinated animal), stimulates an immune response in the animal. Thus, as used herein, an "effective amount" of Rm86Texas protein or the nucleic acid constructs comprising the nucleic acid sequences encoding this protein, is preferably defined as that amount which will elicit a protective immune response against the target tick, which may be either or both of antibody production against the protein or a cell-mediated immune response against the tick, in a treated animal in comparison to an untreated control animal. In a preferred embodiment, an immune response may be demonstrated by production of antibodies against the Rm86Texas protein, by a significant reduction in the percentage of animals infested with the target tick, by a significant reduction in the average number of target ticks on animals, or by a significant reduction in the number of viable eggs or offspring produced by the target ticks present on animals, all in vaccinated animals as compared to an unvaccinated control group (measured at a confidence level of at least 70%, preferably measured at a confidence level of 90%). The actual effective amount will of course vary with the specific vaccine component (protein vaccine or DNA vaccine), the particular animal of interest and its age and size, and the route of administration, and may be readily determined empirically by the practitioner skilled in the art using an antigen dose response assay. By way of example and without being limited thereto, for vaccines administered to small animals (such as dogs and cats) by subcutaneous or intramuscular injection, or with a needle-less device, it is envisioned that typical doses of protein vaccine, may be greater than 0.3 μg protein/animal/dose, preferably between about 0.3 to 1.75 μg protein/animal/dose, while typical doses of DNA vaccine (nucleic acid constructs) may be greater than 100 μg of DNA construct/animal/dose, preferably between about 300 to 800 μg DNA construct/animal/dose. For vaccines administered to large animals (such as deer and horses) by subcutaneous or intramuscular injection, or with a needle-less device, it is envisioned that typical doses of protein vaccine, may be greater than 10 μg protein/animal/dose, preferably between about 50 to 150 μg protein/animal/dose, while typical doses of DNA vaccine (nucleic acid constructs) may be greater than 100 μg of DNA construct/animal/dose, preferably between about 300 to 800 μg DNA construct/animal/dose.

The vaccines (Rm86Texas protein or the nucleic acid constructs comprising the nucleic acid sequences encoding this protein) may be used for the treatment of a broad spectrum of wild or domesticated animals, ranging from pets and companion animals to livestock and large domestic or wild animals. Without being limited thereto, the vaccines are preferably used for the treatment of Cervidae, equine, canines and felines, rodents, and particularly deer (including white-tailed deer and red deer), horses, domestic dogs and cats, and the white-footed mouse. The vaccines may be effectively administered any time after the animal attains immunocompetence. The vaccines may be administered to the subject animal by any convenient route which enables an immune response. However, parenteral injection (e.g., subcutaneous, intravenous, or intramuscular) may be preferred, with intradermal injection being particularly preferred for administration of the DNA vaccines and subcutaneous or intramuscular injection being particularly preferred for administration of the protein vaccines. The vaccine products could also be administered using a needle-less device. In some preferred embodiments, the vaccine may also be administered orally. The vaccine may be administered in a single dose or in a plurality of doses. Dependent upon rearing conditions, the vaccine may be administered in multiple doses, the timing of which may be readily determined by the skilled artisan.

Where the nucleic acid constructs are to be employed for the production of recombinant Rm86Texas protein, a variety of vector-host cell expression systems may be employed. Strains of yeast, particularly *Pichia pastoris*, are preferred. However, the novel invention described here can be applied with numerous host cells that would desirable. Host strains may be of bacterial, fungal, insect cell line, plant, or yeast origin. Ascertaining the most appropriate host-vector system is within the skill of the person in the art.

DNA constructs may be introduced into the appropriate host cell by numerous methods described in the technical and scientific literature. Transformation of bacteria, yeast, or filamentous fungi may be performed using standard techniques. In general, linear or circular DNA constructs may be introduced into the host cell by techniques utilizing protoplast fusion, polyethylene glycol, liposomes, lithium acetate, electroporation, physical damage, biolistic bombardment, or *Agrobacterium* mediated transformation.

Successful transformants may be isolated by using markers, contained on the expression vectors, which confer a selectable trait to the transformed host cell. These may include nutritional selection related to substrate utilization (such as, growth on acetamide containing medium) or prototrophy of a required growth product (such as, arginine, leucine, or uracil). Dominant selectable markers [such as, resistance to ampicillin, G418, hygromycin, and phleomycin, and Zeocin (a composition of bleomycin and phleomycin, Invitrogen, Grand Island, N.Y.)] are also useful in selecting transformants that have taken up the introduced DNA construct.

The DNA construct may be replicated autonomously or integrated into the genome of the host cell. Integration typically occurs by homologous recombination (for example, arginine selectable marker integrating in the chromosomal arginine gene) or at a chromosomal site unrelated to any genes on the DNA construct. Integration may occur by either a single or double cross-over event. It is also possible to have any number of these integration and replication types occurring in the same transformant.

The following exemplary method is intended only to further illustrate the invention and is not intended to limit the scope of the invention which is defined by the claims.

Exemplary Method for Producing Rm86Texas Antigen

The Rm86Texas antigen-encoding sequence was discovered, cloned, and expressed as a recombinant protein in the yeast *Pichia pastoris* using protocols as described in Guerrero et al. (Guerrero F D, Andreotti R, Bendele K G, Cunha R C, Miller R J, Yeater, K et al. *Rhipicephalus* (*Boophilus*) *microplus* aquaporin as an effective vaccine antigen to protect against cattle tick infestations. Parasites Vect 2014; 7:475), the entirety of which is incorporated herein by reference. One hundred larvae from the f37 generation of the Deutsch *R. microplus* strain laboratory colony were collected, frozen while alive, and stored in cold RNAlater-ICE (Ambion, Austin, Tex., USA). The Deutsch strain was started from a few individual engorged females collected from a 2001 *R. microplus* outbreak in Webb County, Tex., USA. Total RNA was isolated from 100 larvae using the ToTALLY RNA kit (Ambion) per the manufacturer's protocol. One microgram of total RNA was used to make single stranded cDNA with the SuperScript III First-Strand Synthesis System kit (Life Technologies, Grand Island, N.Y., USA), designing primers from the complete coding sequence of Bm86 (GenBank Accession No. M29321.1) using Primer3Plus. The Advantage 2 PCR kit (Clontech Laboratories Inc.) was used to amplify the target region using a two-step PCR protocol, which was 95° C. for 1 min, followed by 30 cycles of 95° C. for 30 sec and 68° C. for 2 min, and a final extension time of 3 min at 68° C. The cDNA was diluted to 1:100 for a 50 µl PCR reaction using Bm86 forward 5'-ATGCGTGGCATCGCTTTGTT-3' (SEQ ID NO: 3) and Bm86 reverse 5'-GGTGTTCGATGTAAGCGTGATG-3' (SEQ ID NO: 4) primers (Sigma-Aldrich, The Woodlands, Tex., USA). PCR products were fractionated by agarose gel electrophoresis and post-stained using GelStar® Nucleic Acid Gel Stain (Lonza Rockland, Inc.). The expected 965 bp DNA amplicon was excised from the gel and extracted and purified using the QIAquick Gel Extraction Kit (Qiagen, Valencia, Calif., USA) according to the manufacturer's protocol. The DNA was concentrated using Pellet Paint Co-Precipitant (Novagen/EMD Chemicals Inc., Gibbstown, N.J., USA), polished, ligated and transformed into XL10 Gold Kan Ultracompetent *Escherichia coli* cells using the PCR Script Amp Cloning Kit (Stratagene/Agilent Technologies Inc., Santa Clara, Calif., USA). Individual clones were screened via PCR using internal vector primers and clones producing the expected sized product were used for plasmid DNA preparations with the QIAprep Spin Miniprep Kit (Qiagen) according to manufacturer's instructions. Plasmid DNAs were sequenced on a 3130×1 Genetic Analyzer (Applied Biosystems, Foster City, Calif., USA), using vector and internal sequencing primers such that identities of each nucleotide could be verified on both strands to produce a high quality sequence. Sequences were assembled and analyzed using MacVector with Assembler version 10.0.2 (MacVector Inc., Cary, N.C., USA).

DNA was then prepared for ligation into the *Pichia pastoris* expression vector by restriction enzyme digestion reactions with EcoRI and NotI (Life Technologies) per manufacturer's protocol. The EasySelect *Pichia* Expression Kit vector pPICZ C (Life Technologies), digested with EcoRI and NotI and purified, was ligated onto the Rm86Texas DNA using T4 DNA Ligase (Life Technologies) using the manufacturer's protocol and 70 ng Rm86Texas insert, 45 ng pPICZ C EcoRI/NotI digested vector, and 2.5 unit T4 DNA ligase incubated for 15 hr at 14° C. Five additional units of T4 DNA Ligase were added and the reaction incubated 1 hr at 14° C. OneShot TOP10 competent cells (Life Technologies) were transformed with ligation reaction and plated on low salt LB agar (1% tryptone, 0.5% yeast extract, 0.5% sodium chloride, 1.5% agar) with 25 µg/mL Zeocin™ (Life Technologies). DNA was isolated from resulting colonies using the QIAprep Spin Miniprep Kit (Qiagen). The sequence of both strands of putative positive clone plasmid DNA was verified by DNA sequencing, followed by analysis with MacVector with Assembler version 10.0.2. Five µg of DNA was linearized with SstI (Life Technologies) and used for transformation of freshly prepared electrocompetent *P. pastoris* GS115 strain according to the EasySelect *Pichia* Expression Kit instructions. The Bio-Rad Gene Pulser and Pulse Controller was used with 2 mm cuvettes and pulse settings of 1.5 kV, 200Ω and 25 µFD. Transformation mixtures were plated on YPDS (1% yeast extract, 2% peptone, 2% dextrose, 1 M sorbitol, 2% agar) plates containing 100 µg/mL Zeocin™ and incubated at 30° C. for 4 days to allow colonies to develop. Selected colonies were Mut phenotyped and small-scale expression experiments used to determine the optimal method and conditions for the expression of the recombinant proteins using BMGH (100 mM potassium phosphate pH=6.0, 1.34% yeast nitrogen base with ammonium sulfate without amino acids, $4 \times 10^{-5}$% biotin, 1% glycerol) and BMMH media (BMGH but substituting 0.5% methanol for the 1% glycerol). BMMH cultures were replenished to 0.5% final methanol concentration every 24 hr. Samples were collected at various time points and centrifuged to separate the yeast cells from the culture media supernatant. Recombinant Rm86Texas was localized in the cell pellet sample with maximal expression seen after 12-19 hr of induction growth in BMMH. Intracellular proteins were purified by a protocol similar to that described in the EasySelect *Pichia* Expression Kit manual. Briefly, 100 µl of breaking buffer (50 mM sodium phosphate pH7.4, 1 mM EDTA, 5% glycerol)+1× FOCUS ProteaseArrest (GBioscience, St. Louis, Mo.) was used per cell pellet from a 1 ml culture sample. An equal volume of 0.5 mm acid-washed glass beads was added and the sample vortexed for 30 sec and set on ice for 30 sec. A total of 8 vortex/ice cycles were used, the sample frozen at −80° C., thawed, and 8 more vortex/ice cycles used before a final short centrifugation to clarify the sample. Samples were concentrated in Amicon Ultracel units (Millipore, Billerica, Mass.) and analyzed by denaturing gel electrophoresis under reducing conditions using the NuPAGE Electrophoresis System and NuPAGE 4-12% Bis-Tris gels in the XCell SureLock™ Mini-Cell with 1× NuPAGE MOPS SDS Running Buffer (Life Technologies) according to manufacturer's instructions. Proteins were visualized by staining with Coomassie Brilliant Blue R-250 using a modified Fairbank's method. At this stage, protein identity was verified by Western blotting, taking advantage of the c-myc and 6×-His tag epitopes on the recombinant protein that are provided by the expression vector sequence. The Western-Breeze Chromogenic Kit and Anti-myc-HRP and Anti-His (C-term)-HRP antibodies (Life Technologies) were utilized with standard protocols provided by the supplier. The supplier-provided alkaline phosphatase-conjugated secondary antibody was utilized to enhance sensitivity.

After the optimal clone and growth conditions were determined, a large scale culture of the clone producing the highest amount of recombinant Rm86Texas protein was grown in 25 mL BMGH media in 250 ml baffled flasks in a shaking incubator at 30° C. to an $OD_{600}$=2-6. Cells were harvested by centrifugation and resuspended in BMMH to an $OD_{600}$=1 and returned to the incubator to induce expression. After 19 hr, cells were harvested by centrifugation and the cell pellet frozen at −80° C. Total yeast intracellular protein was extracted similarly as described above for the small-scale expression cell pellet protocol with the exception of using 50 mL Breaking Buffer with 1× Protease Arrest and 10 cycles of 30 sec vortexing followed by 30 sec on ice. The cell pellet lysates were then frozen at −80° C. overnight and thawed followed by 10 vortex/ice cycles. The protein solution was clarified by centrifugation and the resulting solution concentrated using Centricon Plus-70 Centrifugal Filter Devices (Millipore).

Recombinant protein was then purified by native affinity chromatography over a nickel column, making use of the 6×-Histidine tag supplied by the vector sequence and the ProBond Purification System (Life Technologies), using ProBond™ nickel-chelating resin under native conditions according to manufacturer's instructions. The recombinant protein antigen was eluted using 50 mM $NaH_2PO_4$, 0.5 M NaCl, 0.25 M Imidazole, pH=8.0. Following elution, glycerol was added to the protein solution to a final concentration of 50% (v/v), protein concentration quantified by the Bio-Rad Protein Assay Kit I with bovine plasma gamma globulin protein standards, purity of the protein solution verified by polyacrylamide gel electrophoresis as described above, and the sample stored at −20° C. SDS-polyacrylamide gel electrophoresis showed the protein to be 70-90% pure and the stock concentration was 5 mg/ml. Protein identity was confirmed by Western blotting as described above and mass spectrometry analysis performed by Protea Bioscience Group (Morgantown, W. Va.). Prior to the mass spectrometry analysis, the recombinant protein (in 50% glycerol solution described above) was purified by 1-D acrylamide gel electrophoresis, extracted from the gel matrix, and digested with trypsin. The resulting peptides were analyzed by LC-MS/MS using an ABSciex5500 Series QTRAP for tandem MS data acquisition followed by a search for peptide matches to the expected sequence of purified antigen.

A 2022 bp cDNA clone was isolated (GenBank Accession Number KX786647) with the identical sequence as HQ014387 reported by Freeman et al. (Freeman J M, Davey R B, Kappmeyer L S, Kammlah D M, Olafson P U. Bm86 midgut protein sequence variation in South Texas cattle fever ticks. Parasites Vect 2010; 3:101.), the entirety of which is incorporated herein by reference, as Webb1, which was isolated from the f29 generation of a laboratory colony started from an outbreak in Webb County in 2001. Although they did not provide a colony name, it is likely that their colony was the same colony as that currently named as the Deutsch strain, the source for the ticks in our study. The present results indicate that the colony rearing protocols have not introduced any nucleotide changes in the 8 generations since the Webb1 sequence was reported. FIG. 1 shows the amino acids encoded by the translated Rm86Texas sequence and comparisons to the protein coding regions from the Bm86 coding regions that served as the active antigen in the anti-tick vaccines TickGARD (Bm86TICK) and Gavac (Bm86GAV). In FIG. 1, colons are used to indicate identity with the Rm86Texas sequence. The shaded amino acids in the Bm86GAV sequence lines correspond with peptides that Rodriguez et al. (Rodriguez M, Rubiera R., Penichet M, Montesinos R, Cremata J, Falcón V, Sánchez G, Bringas R, Cordovés C, Valdés M, Lleonart R, Herrera L, De la Fuente J. High level expression of the *B. microplus* Bm86 antigen in the yeast *Pichia pastoris* forming highly immunogenic particles for cattle. J Biotech 1994; 33:135-146), the entirety of which is incorporated herein by reference, used for antibody production in their studies and the peptides used in the synthetic peptide anti-tick vaccine reported by Peconick et al. (Peconick A P, Sossai S, Firáo F A, Rodrigues M Q R B, Souza e Silva C H, Guzman F, Patarroyo A M, Vargas M I, Patarroyo J H. Synthetic vaccine (SBm7462) against the cattle tick *Rhipicephalus* (*Boophilus*) *microplus*: Preservation of immunogenic determinants in different strains from South America. Exp Parasitol 2008; 119:37-43), the entirety of which is incorporated herein by reference. The underlined amino acids in the Rm86Texas sequence correspond to peptides on the peptide microarrays that reacted with post-vaccination serum from one of the deer in the following study while the bold font indicates reaction with post-vaccination serum from another deer in the aforementioned study. The 2 amino acid regions that are in bold font are the two peptides from the peptide microarray that reacted with serum from both deer. The double underlined amino acids indicate where overlap occurred between reacting peptides to post-vaccination serum from the first deer. There are 23 amino acid differences between the Rm86Texas sequence and the coding region for the Australian Bm86TICK and the Cuban Gavac vaccine antigens. When these two vaccines were discovered and developed, both the Australian cattle tick and those from the Americas were classified as *Boophilus microplus*. Since then, *Boophilus microplus* was reclassified as *Rhipicephalus* (*Boophilus*)

*microplus* and more recently the Australian populations were reinstated as a separate species, *Rhipicephalus australis*. The full sequence listing of Rm86Texas, and the sequence used in *P. pastoris*, are given in FIG. 2.

For antigen production purposes in *P. pastoris*, the Rm86Texas coding region was altered slightly. The second amino acid was changed from R to G to improve the translation initiation sequence surrounding the initiator methionine. Also, the c-myc epitope and a 6x-histidine tag was directly added to the C-terminus of the Rm86Texas coding region. This added the sequence RPPAYVEQKLISEEDLNSAVDHHHHHH (SEQ ID NO: 5) to the C-terminus. The selected clone for antigen production purposes was a Mut+ phenotype and yielded 46 mg/l of Rm86Texas following the affinity chromatography. FIG. 3 shows gel and Western blot analysis results for Rm86Texas. FIG. 3(A) shows proteins extracted from *P. pastoris* cells prior to (Lane 2; 16 μg cell protein extract) and after (Lane 3; 10 μg eluted protein) nickel affinity chromatography. The polyacrylamide minigel gel was stained by Coomassie Blue and also contains prestained protein molecular weight standards (Lane 1). The arrow indicates the location of a 119 kDa β-galactosidase fusion protein that contains the polyhistidine C-terminus tag and is spiked into the molecular weight standards lane as a positive control for Western blots. FIG. 3(B) shows a Western blot of purified Rm86Texas with Lane 1 containing protein molecular weight standards fused with a polyhistidine tag and Lane 2 containing the same sample as Lane 3 of part A, 10 μg eluted nickel-purified Rm86Texas protein, transferred to nitrocellulose, and probed with anti-His antibody. The arrows indicate the LacZ positive control band in Lane 1 and the Rm86Texas in Lane 2 as detected by the anti-His tag antibody. Note that the image brightness of the photographed nitrocellulose blot was altered in order to facilitate viewing these bands as a Figure. The bands were readily visible on the actual blot. The numbers in both A and B indicate the size of each protein standard in kDa. The calculated molecular weight of Rm86Texas as expressed by the pPICZ expression vector was 74.9 kDa and the observed molecular weight in FIG. 2 was 75 kDa.

Exemplary Method for Vaccine Formulation and Immunization

For vaccines, a formulation of 100 μg of protein antigen per dose in 2 ml volume of antigen plus adjuvant was used. Other antigen concentrations are also envisioned, as would be recognized by one of ordinary skill in the art. The concentration and dosage amounts given herein are meant to be exemplary, and are not limiting. The adjuvant used was Montanide 71 (Seppic, Fairfield, N.J., USA) and the vaccine was formulated by mixing antigen in the purification buffer and using a syringe mixing technique recommended by the adjuvant supplier to prepare a stable water in oil emulsion. Though a particular adjuvant is used, it is envisioned that any suitable adjuvant could be used to formulate the vaccine, as recognized by one of ordinary skill in the art. The deer were vaccinated intramuscularly into the neck with a 1 inch needle at the start of weeks 1, 4 and 7 with adjuvant alone (group 1, control) and Rm86Texas in adjuvant (group 2). Blood samples were drawn from each deer prior to each vaccination and every four weeks following the third vaccination for 24 weeks. Thirty ml of blood was collected from each deer in three 10 ml aliquots, using a 12.5 ml serum separator tube for serum collection along with two other tubes containing EDTA for flow cytometry analysis. Serum was collected after centrifugation and stored at −80° C. Serum antibody titers were determined using an antigen-specific ELISA developed as described below.

Determination of T-Cell and B-Cell Response

The whole blood samples were lysed and leukocytes labeled with antibody to determine the relative proportions of certain cell subsets and the proportion of antigen-specific B cells via flow cytometry analysis. To obtain leukocytes for staining, 10 ml of whole blood was added to 40 ml lysis solution (1.6 M Ammonium Chloride/0.16 M Tris-Cl, pH=7.2) in a 50 ml centrifuge tube and mixed thoroughly until the red blood cells lysed. Tubes were centrifuged at 1700 rpm for 7 min. Supernatant was decanted and cells were resuspended in 50 ml Phosphate-Buffered Saline (PBS) containing 1% Fetal Bovine Serum (FBS). Tubes were centrifuged again at 1700 rpm for 7 min. This cell washing was repeated once more. The final cell pellet was resuspended in an appropriate volume of PBS-1% FBS so there was sufficient volume of cells to add 50 μl per well to a 96-well round-bottomed plate. Fifty μl of PBS-1% FBS was added to appropriate wells as a negative control. The following primary antibodies were added to appropriate wells at 50 μl per well: 1) 2-104, 2) 17D, 3) 2-104, 3C10 and Rm86Texas antigen, and 4) ST8, F10-197 and 17D. Table 1 indicates leukocyte subset specificity for each antibody.

TABLE 1

Proportions of leukocyte subsets in white-tailed deer prior to vaccination.

| 1° antibody | Reactivity | Cell Type Detected | Mean FACS %$^a$ |
| --- | --- | --- | --- |
| 17D | CD4 | Th | 21 ± 3.4 |
| ST8 | CD8 | Tc | 28 ± 2.8 |
| 10-197 | T19 | □□-T | 6.1 ± 1.6 |
| 2-104 | CD72 | B | 18.3 ± 4.5 |
| 3C10 | CD14 | Macrophages | 13.6 ± 3.5 |

$^a$Data represents the mean percentage of cells positive for each antibody ± std. deviation, pooling data from all eight deer sampled prior to vaccination.

After cell addition, the plate was incubated for 10 min at 4° C. and then centrifuged at 1200 rpm for 1-2 min. Supernatant was carefully aspirated from each well and the cells resuspended in 175 μl of PBS-1% FBS and centrifuged at 1200 rpm for 1-2 min. Two more washes and centrifugations were performed before addition of diluted fluorescent antigens and secondary antibodies. Fifty μl of diluted fluorescent Rm86Texas antigen were added to appropriate wells followed by 50 μl of secondary antibodies (GAM-IgG2B-Cy5, GAM-IgM-PE, GAM-IgG1-FITC). Cells were resuspended by use of a plate shaker and then incubated for 10 min at 4° C. Seventy-five μl of PBS-1% FBS were added to each well and the plate centrifuged at 1200 rpm for 1-2 min. Supernatant was aspirated and cells washed with 175 μl PBS-1% FBS and centrifuged at 1200 rpm for 1-2 min. Supernatant was aspirated and cells were resuspended in 100 μl PBS-1% paraformaldehyde and analyzed via flow cytometry to determine the relative proportions of certain cell subsets and the proportion of antigen-specific B cells. One flow cytometry run was performed for each blood sample and the results from all individuals within the same treatment group combined to calculate the treatment group mean and standard deviation.

Figure 4:
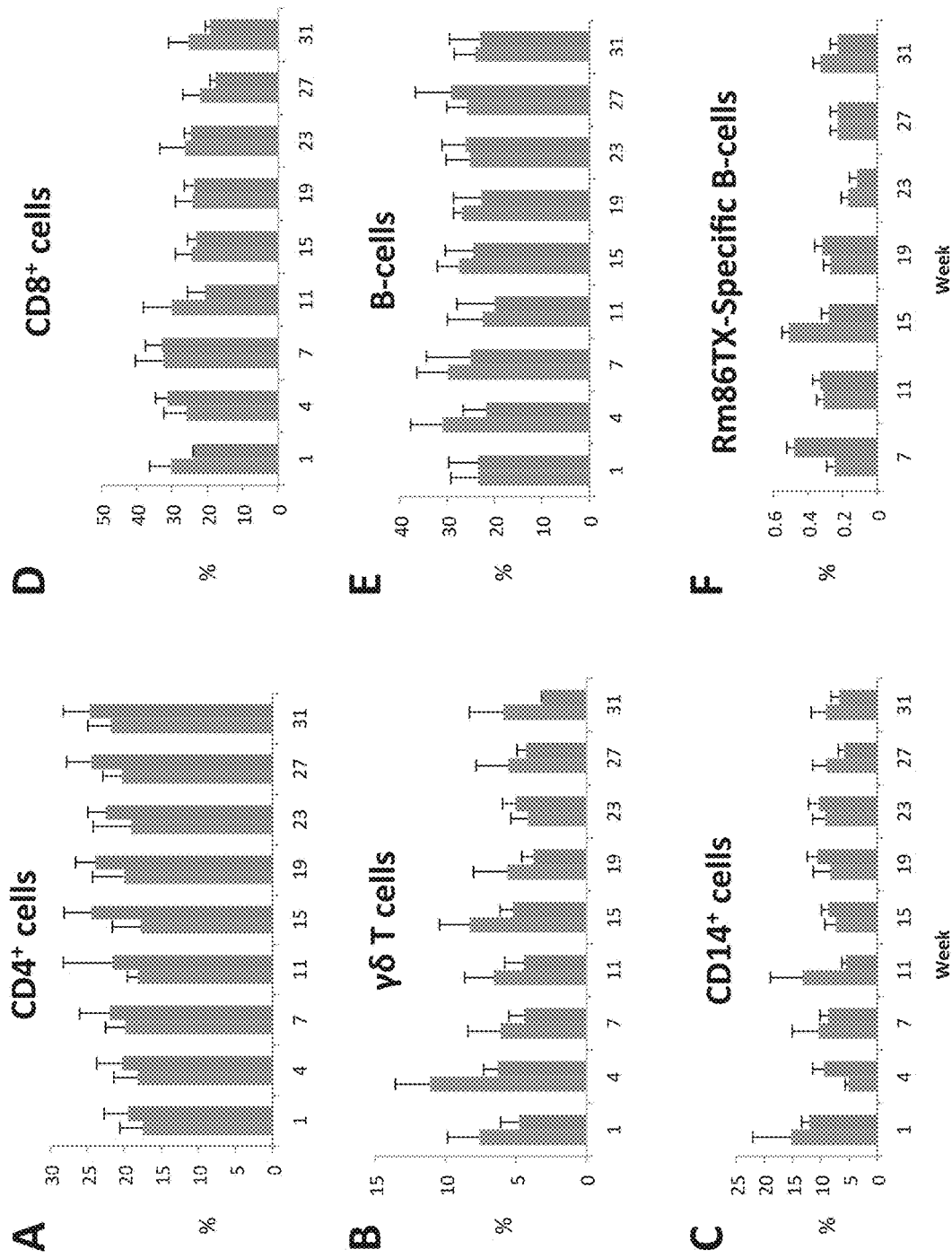
FIG. 4 shows flow cytometry analysis of changes in T cell subsets, B cells, macrophages, and Rm86Texas-specific B cells of white-tailed deer following vaccination.

FIG. 4 shows the changes in $CD4^+$, gamma delta T, $CD14^+$, $CD8^+$, and B cells prior to and following vaccination with the anti-tick vaccine candidate antigen Rm86Texas. Temporal changes in peripheral blood mononuclear cells (PBMC) proportions of (A) $CD4^+$ T-cells, (B) gamma delta T cells, (C) $CD14^+$ monocytes, (D) $CD8^+$ T cells, (E) B cells, and (F) Rm86Texas—specific B cells following vaccination of white-tailed deer with adjuvant only (blue) and Rm86Texas in adjuvant (purple). Data points are shown as mean percentage of cells positive for each diagnostic antibody±standard deviation. Each treatment group consisted of four animals and vaccination occurred on the first day of weeks 1, 4, and 7. There were wide variations among the individual animals, particularly among the control deer, and this is reflected in the standard deviation bars in FIG. 3. There appeared to be greatest overall fluctuations among $CD4^+$ T (FIG. 3A), gamma delta T cells (FIG. 4B), and B cells (FIG. 4E). FIG. 4F shows how Rm86Texas-specific B cell populations fluctuated during the trial. There was a clear increase in Rm86Texas-specific B cells in the week 7 sample, which was taken immediately prior to the third vaccination. Following the week 7 sample, there were very little differences between the control and Rm86Texas vaccinated animals. The clear exception was in the week 15 sample where the control group exhibited the largest reading in the trial. It is noteworthy that the week 11 blood tests revealed that 2 of the control deer had become seropositive for Epizootic Hemorrhagic Disease Virus (EHDV) and 1 had become seropositive for Bluetongue Virus. This was in addition to the other individual in the control group that was found weakly seropositive for Bluetongue Virus at the start of the trial and remained so throughout. One of the EHDV positive control deer eventually died in week 12.

Determination of Antibody Levels

Serum antibody titers were determined using an antigen-specific ELISA. Antigen was diluted in 0.05 M carbonate-bicarbonate buffer, pH=9.6 at a concentration of 10 μg/ml. Fifty μl of this coating antigen mixture were added to each well of a micro-ELISA plate, covered with an acetate lid and incubated overnight at 4° C. The coating antigen mixture was removed and 100 μl of Blotto blocking solution added and incubated at room temperature for 1 hr. The blocking solution was removed and the plate washed 5 times with 200 μl per well of Tris-Buffered Saline (TBS) pH 7.5, 0.05% Tween-20 containing 10% blocking solution. One hundred μl of test sera was added to the plate at 1:50, 1:100, 1:200, 1:400, 1:800, 1:1600, 1:3200, and 1:6400 dilutions and incubated 2-3 hr at room temperature. The plate was washed 5 times with 200 μl per well of TBS-Tween-Blotto. One hundred μl of peroxidase-labeled rabbit anti-deer IgG (KPL, Gaithersburg Md.), diluted 1:5000 in TBS-Tween-Blotto, was added to each well and incubated one hr at room temperature. The plate was washed five times with 200 μl per well of TBS-Tween-Blotto. One hundred μl of substrate solution was added to each well and incubated for 15 min in the dark. Finally, 50 μl of stop solution (2 N Sulfuric Acid) were added to each well and absorbance measured at 450 nm. Endpoint titer was determined using the statistical method described by Frey et al. (Frey A, Di Canzio J, Zurakowski D. A statistically defined endpoint titer determination method for immunoassays. J Immunolog Meth 1998; 221:35-41), the entirety of which is incorporated herein by reference. The cutoff absorbance value was determined by calculating the absorbance value mean from readings taken from serum from all 8 animals prior to the first vaccination. For the remaining serum sample time points, each serum was tested individually and the results from all individuals within the same treatment group combined to calculate the treatment group mean and standard deviation.

Figure 5:
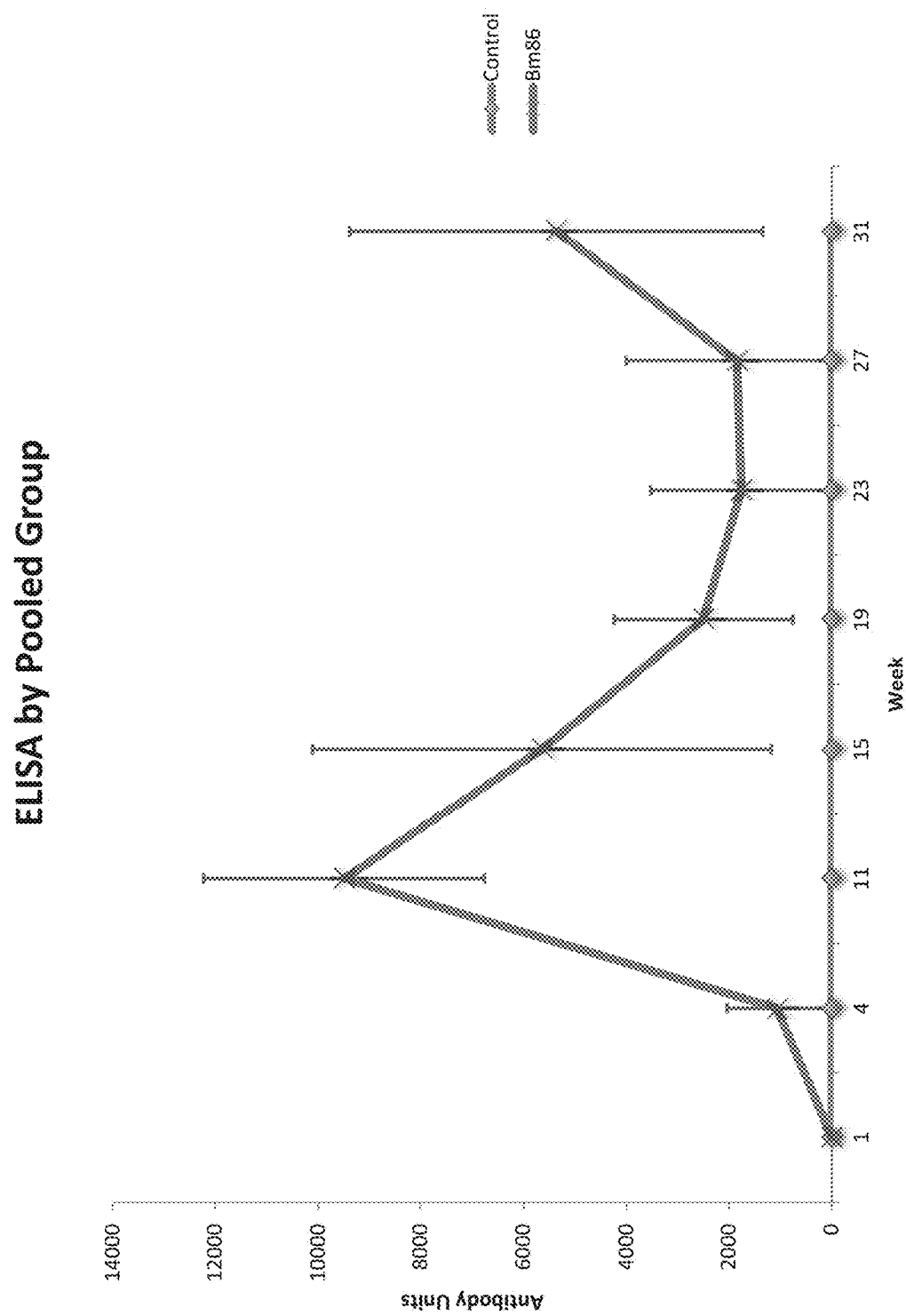
FIG. 5 shows ELISA titers of Rm86Texas-specific antibodies in vaccinated deer and in a control group.

Following the third vaccination, the Rm86Texas-vaccinated deer had mounted a robust antibody response, as shown in FIG. 5. Reciprocal mean titers of Rm86Texas-specific antibodies following vaccination of white-tailed deer with adjuvant only (blue) and Rm86Texas in adjuvant (purple) are shown. Each data point represents the mean of 4 animals±standard deviation. Peak antibody titer against Rm86 was noted at week 11, 4 weeks after the third vaccination, which indicates a boost in immunity was achieved with the third vaccination. A drop in antibody titer was found at week 15 and continued as a gradual decrease until week 23. At week 27, the antibody titer of the Rm86Texas vaccinated group showed a slight increase which continued in the week 31 sample. Deer vaccinated with adjuvant alone showed no significant antibody response to Rm86Texas antigen. Carreon et al. (Carreon D, Perez de la Lastra J M, Almazan C, Canales M, Ruiz-Fons F, Boadella M, et al. Vaccination with BM86, subolesin and akirin protective antigens for the control of tick infestations in white tailed deer and red deer. Vaccine 2012; 30:273-279.), the entirety of which is incorporated herein by reference, reported trials in which white-tailed deer were vaccinated three times with a Bm86-based vaccine and then artificially infested with *R. microplus*. These deer produced a significant antibody response that persisted for at least 6 weeks following the final vaccination and a vaccine efficacy of 76% resulted. In the present invention, the deer immune response with vaccination to Rm86Texas persisted for at least 9 weeks beyond the final vaccination (FIG. 5).

Epitope Mapping

Epitope mapping was conducted by PEPperPRINT GmbH (Heidelberg, Germany) using proprietary protocols. Briefly, the entire Rm86Texas protein coding sequence was translated into 15 aa peptides with a peptide-peptide overlap of 14 aa. The total of 648 different synthesized peptides were spotted in duplicate onto microarrays surrounded by 88 spots each of FLAG (DYKDDDDKGG, SEQ ID NO: 6) and human influenza hemaglutinin A (YPYDVPDYAG, SEQ ID NO: 7) as control epitope tag peptides. Arrays were tested for background interactions by a 10 min incubation with incubation buffer (PBS, pH 7.4 with 0.05% Tween 20, 10% Rockland blocking buffer) followed by 60 min of blocking with 10% Rockland buffer, and 60 min incubation with secondary rabbit anti-deer IgG (H+L) labelled with IRDye680 at 1:5000 dilution. Sera from 2 deer from the Rm86Texas-vaccinated group, deer #88 and #91, were used for epitope mapping with each serum tested with a set of 4 arrays. Serum was collected just prior to vaccination and at Week 11 of the study, which was 4 weeks after the 3rd vaccination. The peptide microarrays with the antigen-derived peptides were blocked for 1 hr with Rockland blocking buffer, then incubated for 16 hr at 4° C. and shaking at 500 rpm with the pre-vaccination or the post-vaccination serum at dilutions of both 1:1000 and 1:100 with each dilution done on separate arrays. This entire experiment was done for each of the two deer sera and also replicated once. Following staining with the IRDye680-labelled secondary rabbit anti-deer IgG antibody, arrays were read with a LI-COR Odyssey Imaging System (LI-COR Biotechnology-GmbH, Hornburg, Germany) and quantified with PepSlide Analyzer (SICASYS Software GmbH, Heidelberg, Germany).

Peptide microarrays following incubation with pre- and post-vaccination serum are shown in FIG. 6. Blood serum was collected from one deer immediately prior to the first vaccination and 4 weeks after the third vaccination with Rm86Texas antigen. Washed and blocked peptide microarrays were incubated with either pre-vaccination serum or post-vaccination serum at a dilution of 1:1000. Following incubation with labelled secondary antibody, the array dye signals were developed and analyzed to identify peptide that bound to antibody from the deer serum.

The results of the epitope mapping indicated that an antibody response specific to Rm86Texas was detected.

Immunization Against *Amblyomma americanum*

The Rm86Texas antigen may be used as a vaccine against other non-related species of tick. For example, Rm86Texas may be effective to control ticks of the species *Amblyomma americanum*. In an exemplary embodiment, ticks were fed blood serum taken from vaccinated deer according to the following protocol:

Groups of adult female lone star ticks (*A. americanum*) were placed upside-down on a strip of sticky tape secured on a standard glass slide. The glass slide was then secured to the lid of a Petri dish (14 cm diameter). A strip of utility wax was placed on the Petri dish lid at a distance of 4 cm from the ticks to help secure capillary tubes. A Fisher brand capillary tube (inner diameter 1.1 mm) filled with serum was placed over the mouthparts of each tick. The Petri dish lid was then placed in a mini digital incubator, where the temperature was maintained at 37° C. and relative humidity was maintained at 75-80%. Each group was fed a serum from one of (a) a pre-vaccinated deer, (b) deer injected with adjuvant only, (c) deer immunized with Rm86Texas, and (d) cattle blood (commercially obtained). The deer were treated according to the above-described methods, and the sera were taken immediately prior to a third vaccination. Ticks were fed for 5 days and examined for mortality at 3, 5, and 7 days post feeding. The mean, standard deviation, and standard error were calculated for each group.

Results of the above study are given in Table 2 below:

TABLE 2

| | Mortality rates of the Lone Star Tick fed by immunized serum | | | | | | | | |
|---|---|---|---|---|---|---|---|---|---|
| | % Mortality after 3 days | | | % Mortality after 5 days | | | % Mortality after 7 days | | |
| Serum | Mean | Stdev | Stderr | Mean | Stdev | Stderr | Mean | Stdev | Stderr |
| Pre-vaccination | 33.3 | 5.8 | 3.3 | 43.3 | 11.5 | 6.7 | 43.3 | 11.5 | 6.7 |
| Adjuvant only | 30.0 | 17.3 | 10.0 | 40.0 | 17.3 | 10.0 | 46.7 | 15.3 | 8.8 |
| Rm86Texas | 60.0 | 10.0 | 5.8 | 83.3 | 15.3 | 8.8 | 93.3 | 5.8 | 3.3 |
| Cattle blood | 6.7 | 5.8 | 3.3 | 16.7 | 15.3 | 8.8 | 20.0 | 17.3 | 10.0 |

As is clear from the data in Table 2, deer serum from deer vaccinated with Rm86Texas was effective at killing ticks compared to the control groups.

Further Embodiments

It is envisioned that a vaccine formulated with Rm86Texas, as disclosed herein, may be modified for one or more purposes. For example, a vaccine may include only Rm86Texas as the sole antigen, or a combination of Rm86Texas and another antigen. Further, it is envisioned that a vaccine containing Rm86Texas may be effective against not only *R. microplus*, but also other tick species, such as, for example, *Ixodes scapularis* (also known as the deer tick), and *Amblyomma americanum* (also known as the lone star tick), as provided for the in the example given herein. For example, Rm86Texas may be combined with RmAQP1, or aquaporin 1, to achieve this result.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method of reducing tick infestations in animals comprising administration of a vaccine composition to a non-bovine animal,
wherein said vaccine composition comprises an immunogenic Rm86Texas protein and a pharmaceutically acceptable carrier,
wherein said Rm86Texas protein is in an amount effective to stimulate an immune response in said animal to said tick,
wherein said Rm86Texas protein consists of amino acids 17-624 of SEQ ID: 1, and
wherein said tick is selected from the group consisting of *Ixodes scapularis* and *Amblyomma americanum*.

2. The method of claim 1, wherein said animal is selected from the group consisting of canines, felines, equine, and Cervidae.

3. The method of claim 2, wherein said animal is selected from the group consisting of domestic cats, domestic dogs, and deer.

4. The method of claim 3, wherein said animal is a deer.

5. The method of claim 4, wherein said animal is one of a white-tailed deer or a red deer.

6. The method of claim 1, wherein said vaccine composition further comprises an adjuvant.

7. A method of reducing the incidence of tick infestations in animals, comprising administering a vaccine composition to a non-bovine animal,
wherein said vaccine composition comprises the nucleic acid construct and a pharmaceutically acceptable carrier,
wherein said nucleic acid construct comprises a nucleic acid sequence encoding an Rm86Texas protein, operatively linked to one or more expression control sequences, and is administered in an amount effective to stimulate an immune response in said animal to said tick,
wherein said Rm86Texas protein consists of amino acids 17-624 of SEQ ID: 1, and
wherein said tick is selected from the group consisting of *Ixodes scapularis* and *Amblyomma americanum*.

8. The method of claim 6, wherein said animal is selected from the group consisting of canines, felines, equine, and Cervidae.

9. The method of claim 8, wherein said animal is selected from the group consisting of domestic cats, domestic dogs, and deer.

10. The method of claim 9, wherein said animal is a deer.

* * * * *